(12) United States Patent
Shan et al.

(10) Patent No.: US 7,491,504 B2
(45) Date of Patent: Feb. 17, 2009

(54) METHOD FOR DETECTING OVARIAN CANCER

(75) Inventors: Lian Shan, Broadview Heights, OH (US); Stanley L. Hazen, Gates Mills, OH (US)

(73) Assignees: Frantz Biomarkers, LLC, Mentor, OH (US); The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 11/595,634

(22) Filed: Nov. 10, 2006

(65) Prior Publication Data

US 2007/0196875 A1 Aug. 23, 2007

Related U.S. Application Data

(60) Provisional application No. 60/738,849, filed on Nov. 22, 2005.

(51) Int. Cl.
*G01N 33/574* (2006.01)
(52) U.S. Cl. .................................... 435/7.25
(58) Field of Classification Search ........................ None
See application file for complete search history.

(56) References Cited

U.S. PATENT DOCUMENTS

| | | | |
|---|---|---|---|
| 5,776,753 A | 7/1998 | Hillman et al. | |
| 6,500,633 B1 | 12/2002 | Compton et al. | |
| 6,830,932 B1 * | 12/2004 | Danne et al. | 436/86 |
| 2002/0123084 A1 * | 9/2002 | Mills et al. | 435/7.23 |
| 2002/0150955 A1 | 10/2002 | Mills et al. | |
| 2004/0137541 A1 | 7/2004 | Mills et al. | |
| 2004/0143461 A1 | 7/2004 | Watkins | |

OTHER PUBLICATIONS

Merchant, T.E., Kasimos, J.N., De Graaf, P.W., Minsky, B.D., Gierke, L.W., and Glonek, T. Phospholipid profiles of human colon cancer using 31P magnetic resonance spectroscopy. International Journal of Colorectal Disease, 1991. vol. 6, pp. 121-126.*
Borsche, T. Plasmalogen levels in serum from patients with imaired carbohydrate or lipid metabolism and in elderly subjects with normal metabolic values. Archives of Gerontology and Geriatrics, 2001. vol. 32, pp. 283-294.*
U.S. Appl. No. 11/601,076, filed Nov. 17, 2006, Confirmation No. 6866.
Stevens et al., "Class F Thy-1-negative Murine Lymphoma Cells Are Deficient in Ether Lipid Biosynthesis," *J. Biol. Chem.*, Sep. 1990, vol. 265, No. 26, pp. 15653-15658.
Zoeller et al., "Isolation of Animal Cell Mutants Deficient in Plasmalogen Biosynthesis and Peroxisome Assembly," *Proc. Natl. Acad. of Sci. of U.S.A.*, Jul. 1986, vol. 83, pp. 5170-5174.
Hale et al., "The selective activation of the cardiac sarcolemmal sodium-calcium exchanger by plasmalogenic phosphatidic acid produced by phospholipase D," *FEBS Letters*, Jan. 1998, 422 (2), pp. 247-251.

Petricoin et al., Use of proteomic patterns in serum to identify ovarian cancer, *The Lancet*, Feb. 2002, 359 (9306), pp. 572-577.
Zhu et al., "Detection of cancer-specific markers amid massive mass spectral data," *PNAS USA*, Dec. 2003, 100 (25), pp. 14666-14670.
Zhen Zhang et al., "Three Biomarkers Identified from Serum Proteomic Analysis for the Detection of Early Stage Ovarian Cancer," *Cancer Research*, 64, 5882-5890, Aug. 15, 2004.
Han et al., "Diabetes-induced changes in specific lipid species in rat myocardium," *The Biochemical Journal*, (2000), vol. 352 (Ptl) : 79-89.
Dueck et al., "The modulation of choline phosphoglyceride metabolism in human colon cancer," *Molecular and Cellular Biochemistry*, (1996), vol. 162 (2) : 97-103.
Morita et al., "Phospholipid turnover in the inflamed intestinal mucosa: Arachidonic acid-rich phosphatidyl/plasmenyl-ethanolamine in the mucosa in inflammatory bowel disease," *Journal of Gastroenterology*, (1999), vol. 34 (1) : 46-53.
Zhu et al., "Molecular species composition of glycerophospholipids in rat sciatic nerve and its alteration in streptozotocin-induced diabetes," *Biochimica et Biophysica Acta.*, (1993), vol. 1168 (1) : 1-12.
Yavin et al., "Docosahexaenoic Acid Abundance in the Brain: A Biodevice to Combat Oxidative Stress," *Nutr. Neuroscience*, (2002), vol. 5 (3), 149-157.
Rapport and Alonzo, "Identification of Phosphatidal Choline as the Major Constituent of Beef Heart Lecithin," *J. Biol. Chem.*, (1955), 217 : 199-204.
Morikawa et al., "A Simple and Sensitive Determination for Plasmalogen Lysophosphatidylethanolamine in Rabbit Platelets," *Thrombosis Research*, (1989), 55: 427-438.
Shaikh, "Assessment of Various Techniques for the Quantitative Extraction of Lysophospholipids from Myocardial Tissues," *Analytical Biochemistry*, (1994), 216:313-321.
Engelmann et al., "Plasmalogen phospholipids as potential protectors against lipid peroxidation of low density lipoproteins," *Biochem. Biophys. Res. Commun.*, (1994), vol. 204, No. 3, 1235-1242.

(Continued)

*Primary Examiner*—Misook Yu
*Assistant Examiner*—Mark Halvorson
(74) *Attorney, Agent, or Firm*—Frishauf, Holtz, Goodman & Chick, P.C.

(57) ABSTRACT

A method of detecting ovarian cancer in a female test subject comprising determining the amount of plasmenyl-PA or a biomarker having a mass charge ratio of approximately 655.3 in a sample of a bodily fluid taken from the female test subject and comparing the amount of plasmenyl-PA (or the biomarker) in the sample of the bodily fluid taken from the female test subject to a range of amounts of plasmenyl-PA (or the biomarker) found in samples of bodily fluids taken from a group of normal female subjects of the same species as the female test subject and lacking ovarian cancer, whereby a lower amount of the plasmenyl-PA (or the biomarker) in the sample of the bodily fluid taken from the female test subject indicates the presence of ovarian cancer.

9 Claims, 9 Drawing Sheets

OTHER PUBLICATIONS

Lee, "Biosynthesis and possible biological functions of plasmalogens", *Biochim. Biophys. Acta*, (1998), 1394:129-145.

Sindelar et al., "The protective role of plasmalogens in iron-induced lipid peroxidation", *Free Radical Biol. Med.*, (1999), 26:318-324.

Confurius and Zwaal, "The Enzymatic Synthesis of Phosphatidylserine and Purification by CM-Cellulose Column Chromatography," *Biochim. Biophys. Acta*, (1977), 488: 36-42.

Merchant et al., "Esophageal cancer phospholipids correlated with histopathologic findings: a $^{31}$P NMR study", *NMR Biomed.*, (1999), 12(4):184-188.

Merchant et al., "$^{31}$P magnetic resonance phospholipid profiles of neoplastic human breast tissues", *Br J Cancer*, 1991), 63(5):693-698.

Leung and Sun, "Acyl Group Composition of Membrane Phospholipids in Mammary Tissues and Carcinoma Induced by Dimethylbenz (a) Anthracene," *Proc. Soc. Exp. Biol. Med.*, 152 (4):671-676.

Albert and Anderson, Ether-linked glycerolipids in human brain trumors, *Lipids*, (1977), 12 (2):188-192.

Tamiya-Koizumi et al., "Lipid composition of the plasma membrane isolated from hyperplastic nodules of rat liver", *J. Biochem.*, (1985), 97 (3):773-779.

Koizumi et al., Comparative study of the phospholipid composition of plasma membranes isolated from rat primary hepatomas induced by 3'-methyl-4-dimethylaminoazobenzene and from normal growing rat livers, *Cancer Res.*, (1980), 40 (3):909-913.

Koizumi et al., "Rapid isolation and lipid characterization of plasma membranes from normal and malignant lymphoid cells of mouse," *Biochim. Biophys Acta.*, (1981), 649 (2):393-403.

Kuliszkiewicz-Janus et al., "Application of $^{31}$P MRS to the analysis of phospholipid changes in plasma of patients with acute leukemia", *Biochim. Biophys Acta.*, (2005), 1737 (1): 11-15.

Farooqui and Horrocks, "Plasmalogens: workhorse lipids of membranes in normal and injured neurons and glia", *Neuroscientist*, (2001), 7 (3):232-45.

English-language International Preliminary Report on Patentability and Written Opinion of the International Searching Authority, dated Jun. 5, 2008 for International Application PCT/US2006/043893 filed Nov. 22, 2006; Applicants: Frantz Biomarkers, LLC et al.

* cited by examiner

METHOD FOR DETECTING OVARIAN CANCER

CROSS-REFERENCE TO RELATED APPLICATION

This application claims the benefit under 35 USC 119(e) of Provisional application Ser. No. 60/738,849 filed Nov. 22, 2005.

BACKGROUND OF THE INVENTION

1. Field of the Invention

The invention concerns a non-invasive method for detecting or screening for ovarian cancer in a female test subject. More particularly, the invention relates to a method for detecting ovarian cancer in a female test subject by determining the amount of a plasmenyl-PA in a sample of bodily fluid taken from the female test subject.

2. Background Information

Ovarian cancer is one of the deadliest cancers for women, due to its high fatality rate. In the United States, in 2005, it was estimated that 22,000 women would be diagnosed with ovarian cancer and 16,000 women would die of ovarian cancer. Unfortunately, heretofore, only 25% of ovarian cancer patients were diagnosed at stage I. Most of the patients were diagnosed at an advanced stage, stage III or IV, at which the 5-year survival rate decreases to 20 to 25% from 95% at stage I.

Presently, the most commonly used biomarker for diagnosing ovarian cancer is CA-125, a group of surface glycoproteins with uncertain biological function. Although CA-125 is elevated in 82% of women with advanced ovarian cancer, it has very limited clinical application for the detection of early stage disease, exhibiting a positive predictive value less than 10%. The addition of ultrasound improves the positive predictive value to 20%, which is still too low to meet the requirement for ovarian cancer detection. Developing a clinical test to diagnose ovarian cancer with high sensitivity and specificity at the early stage has become the most urgent issue in battling this refractory disease.

Frequently, the detection of cancer depends upon the detection and inspection of a tumor mass, which has reached sufficient size to be detected by physical examination. The detection of molecular markers of carcinogenesis and tumor growth can solve many of the problems associated with the physical examination of tumors. Samples taken from the patient for screening by molecular techniques are typically blood or urine, and thus require minimally invasive techniques. Thus, they can be used on a regular basis to screen for cancers. Furthermore, because molecular markers often appear before the tumor reaches a detectable size, it is possible to detect cancers at very early stages in the progression of the disease.

Biomarkers identified from serum proteomic analysis for the detection of ovarian cancer are discussed in Z. Zhang et al., *Cancer Research*, 64, 5882-5890, Aug. 15, 2004.

Methods for detecting cancer associated with elevated concentrations of lysophospholipids have been described in US 2002/0123084 and US 2002/0150955.

U.S. Pat. No. 6,500,633 discloses a method of detecting carcinomas by measuring the level of a glycerol compound, such as glycerol-3-phosphate, in a plasma, serum or urine specimen from a patient.

SUMMARY OF THE INVENTION

It is an object of the invention to provide a non-invasive method for detecting or screening for ovarian cancer in a female test subject.

One embodiment of the invention concerns a method of detecting or screening for ovarian cancer in a female test subject comprising:

determining the amount of plasmenyl-PA in a sample of a bodily fluid taken from a female test subject, and comparing the amount of plasmenyl-PA in the sample of the bodily fluid taken from the female test subject to a range of amounts of plasmenyl-PA found in samples of the bodily fluids taken from a group of normal female subjects of the same species as the female test subject and lacking ovarian cancer, whereby a lower amount of the plasmenyl-PA in the sample of the bodily fluid taken from the female test subject indicates the presence of ovarian cancer.

Another embodiment of the invention also relates to a method of detecting or screening for ovarian cancer in a female test subject comprising:

determining the amount of a biomarker having a mass charge ratio of approximately 655.3 in a sample of a bodily fluid taken from a female test subject, and comparing the amount of the biomarker in the sample of the bodily fluid taken from the female test subject to a range of amounts of the biomarker found in samples of the bodily fluid taken from a group of normal female subjects of the same species as the female test subject and lacking ovarian cancer, whereby a lower amount of the biomarker in the sample of the bodily fluid taken from the female test subject indicates the presence of ovarian cancer.

A further embodiment of the invention concerns a method for monitoring ovarian cancer in a female test subject over time comprising:

(a) determining the amount of plasmenyl-PA in a sample of a bodily fluid taken from a female test subject at a first time, (b) determining the amount of plasmenyl-PA in a sample of the bodily fluid taken from said female test subject at a second time, which is a later time than the first time, (c) comparing the amounts of plasmenyl-PA in step (a) and step (b) to determine whether there has been an increase or a decrease in the amount of plasmenyl-PA in the sample taken from the female test subject at the later time relative to the amount of the plasmenyl-PA in the sample taken from the female test subject at the first time, whereby a decrease in the amount of the plasmenyl-PA in the sample taken from the female test subject at the later time indicates the presence of, or worsening of, ovarian cancer, or an increase in the amount of plasmenyl-PA in the sample taken from the female test subject at the later time indicates an absence, or improvement of, ovarian cancer.

A still further embodiment of the invention relates to a method for monitoring ovarian cancer in a female test subject over time comprising:

(a) determining the amount of a biomarker having a mass charge ratio of approximately 655.3 in a sample of a bodily fluid taken from a female test subject at a first time, (b) determining the amount of the biomarker in a sample of the bodily fluid taken from said female test subject at a second time, which is a later time than the first time, (c) comparing the amounts of the biomarker in step (a) and step (b) to determine whether there has been an increase or a decrease in the amount of the biomarker in the sample taken from the female test subject at the later time relative to the amount of the biomarker in the sample taken from the female test subject at the first time, whereby a decrease in the amount of the biomarker in the sample taken from the female test subject at the later time indicates an increase in the presence of or worsening of, ovarian cancer, or an increase in the amount of plasmenyl-PA in the sample taken from the female test subject at the later time indicates an absence, or improvement of ovarian cancer.

DETAILED DESCRIPTION OF THE INVENTION

Figure 1:
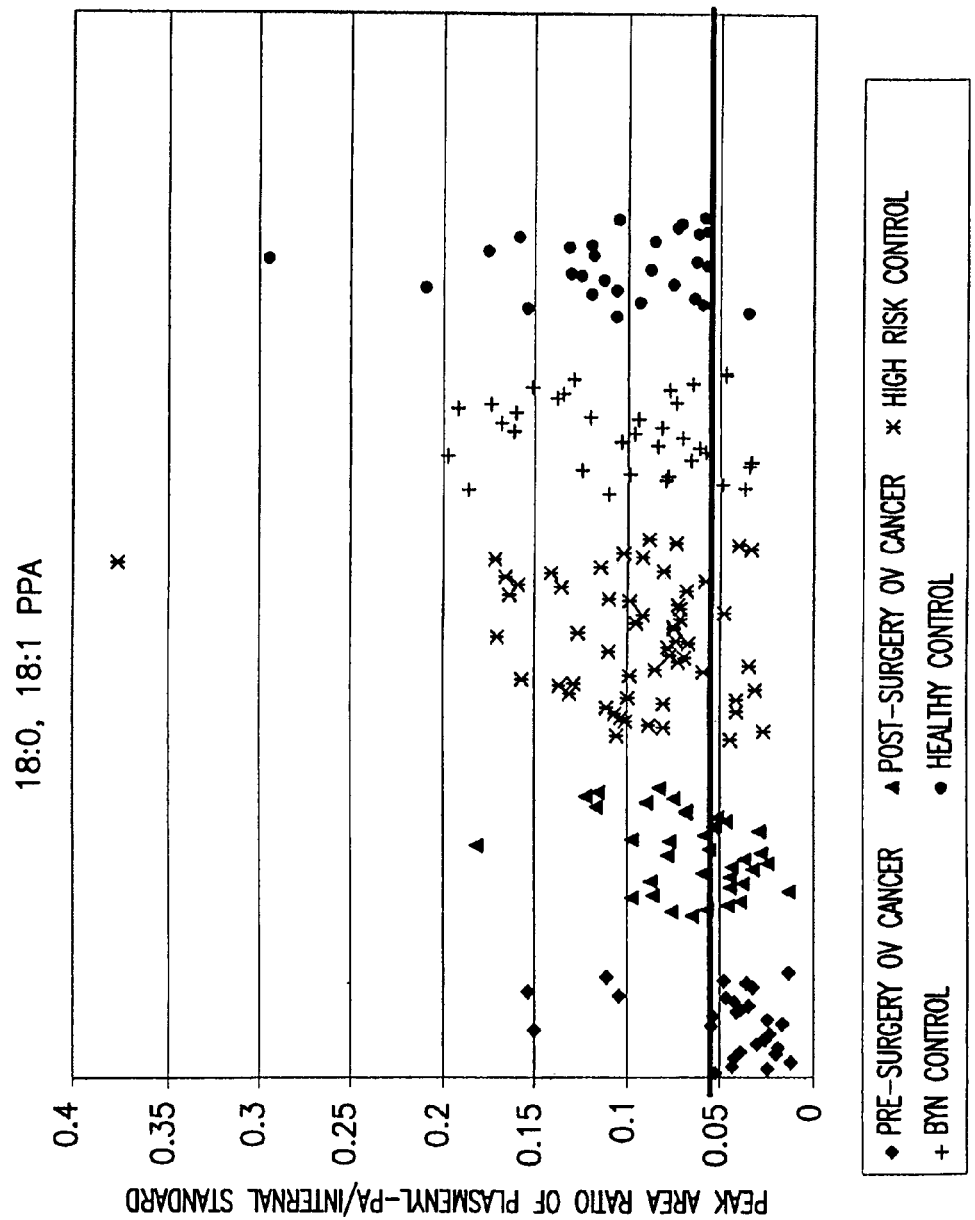
FIG. 1 is a graphical representation showing the levels of 16:0, 18:2 plasmenyl-PA (PPA) in the following 196 serum samples: pre-surgery ovarian ("ov") cancer, post-surgery ovarian ("ov") cancer, high-risk control, benign gynecological disease ("BYN") control and healthy control.
Figure 2:
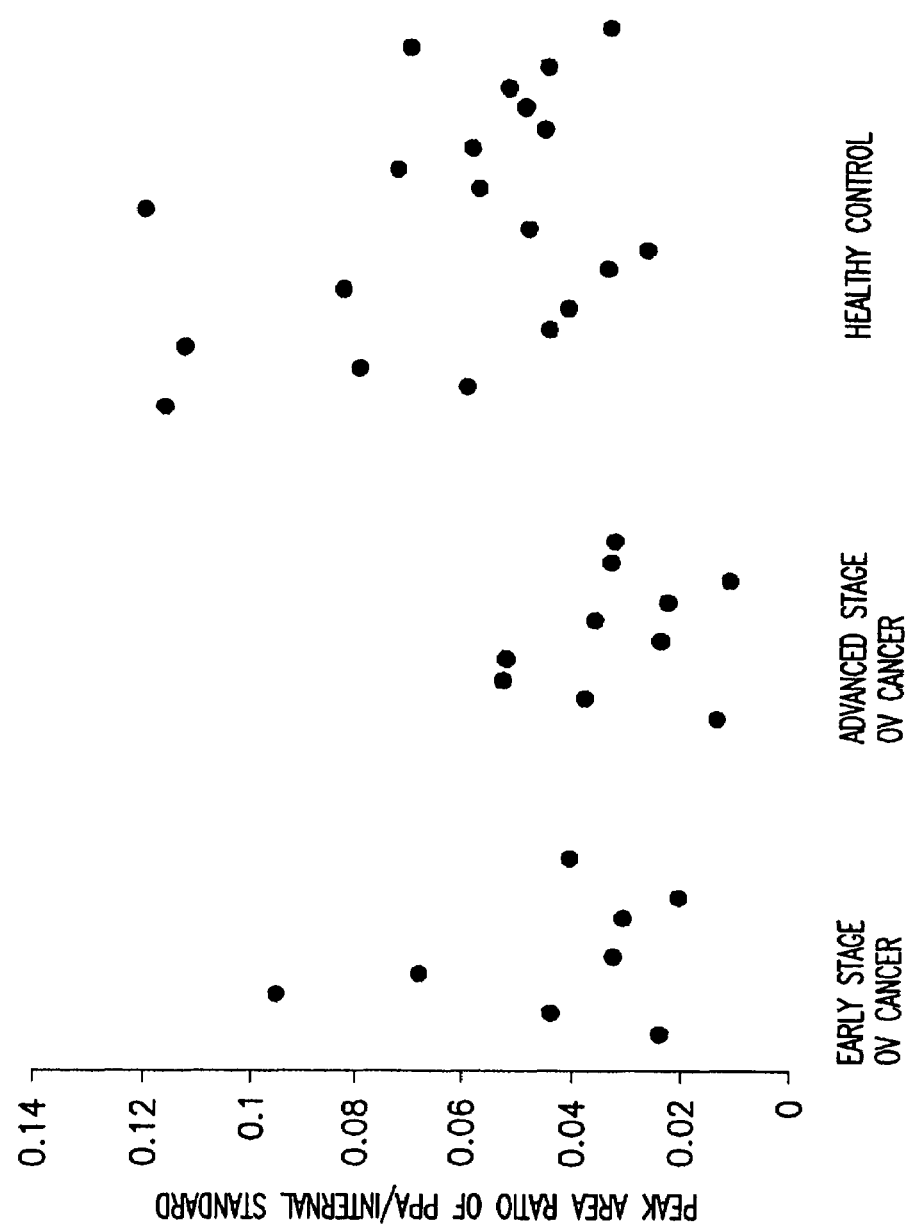
FIG. 2 is a graphical representation of the levels of 16:0, 22:6 PPA in the following 38 serum samples: early stage ovarian cancer ("ov"), advanced stage ov cancer and healthy control.
Figure 3:
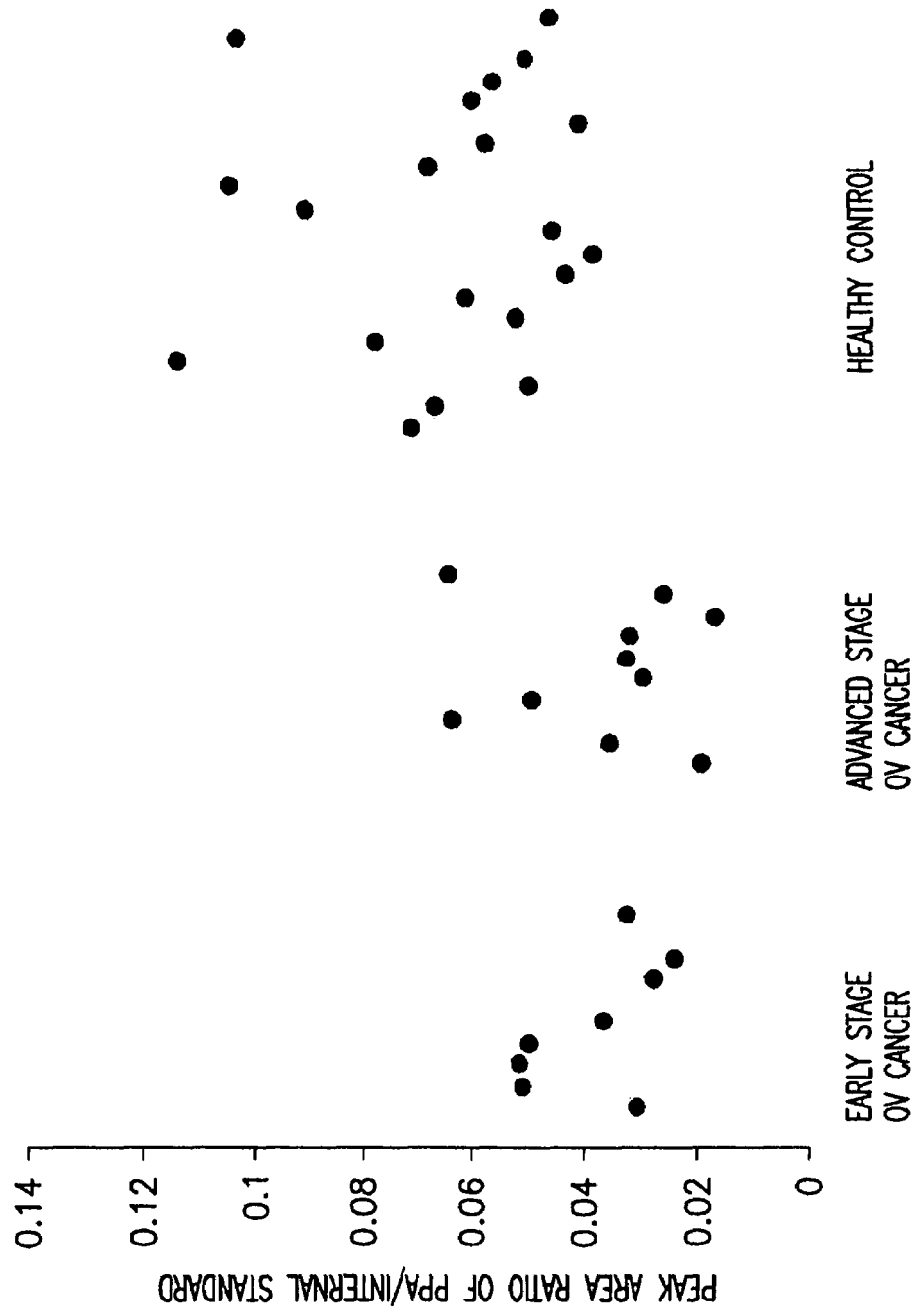
FIG. 3 is a graphical representation of the levels of 16:0, 20:4 PPA in the following 38 serum samples: early stage ov cancer, advanced stage ov cancer and healthy control.
Figure 4:
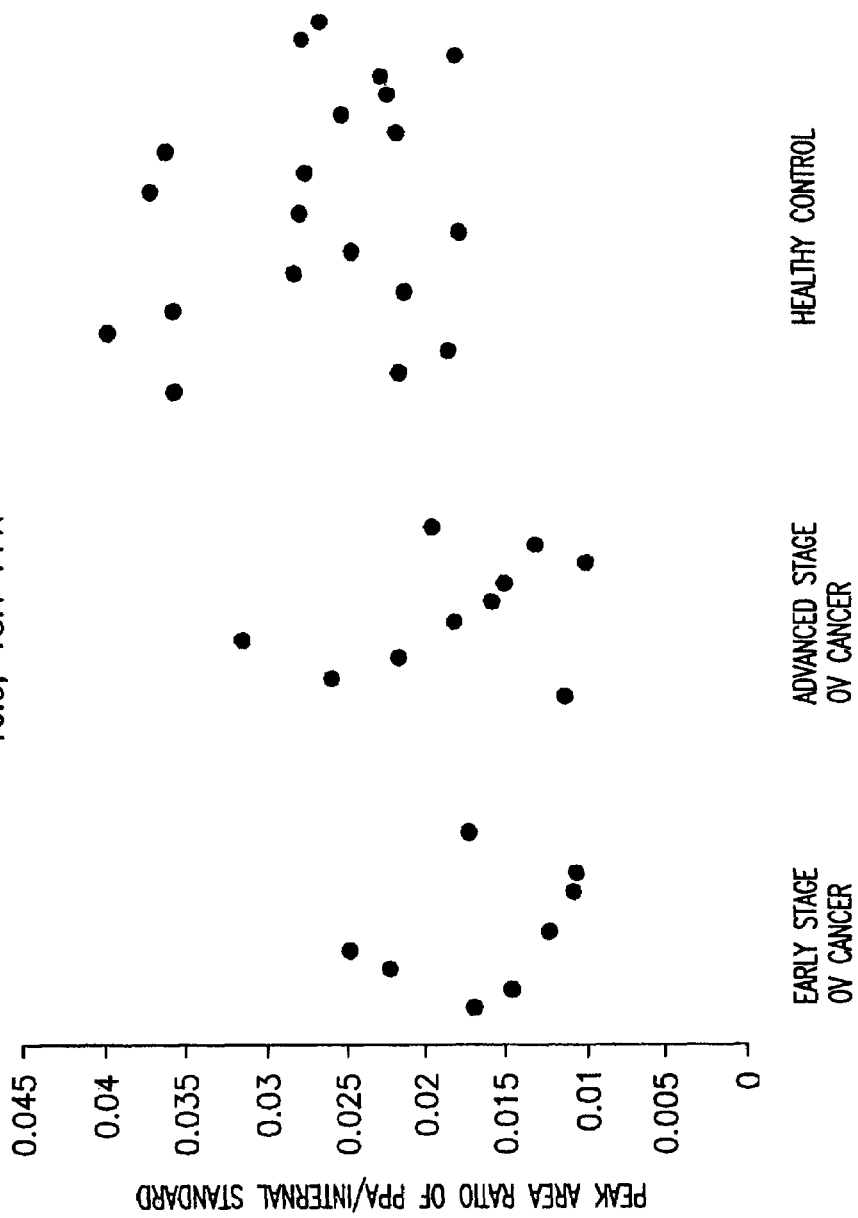
FIG. 4 is a graphical representation of the levels of 16:0, 18:1 PPA in the following 38 serum samples: early stage ov cancer, advanced stage ov cancer and healthy control.
Figure 5:
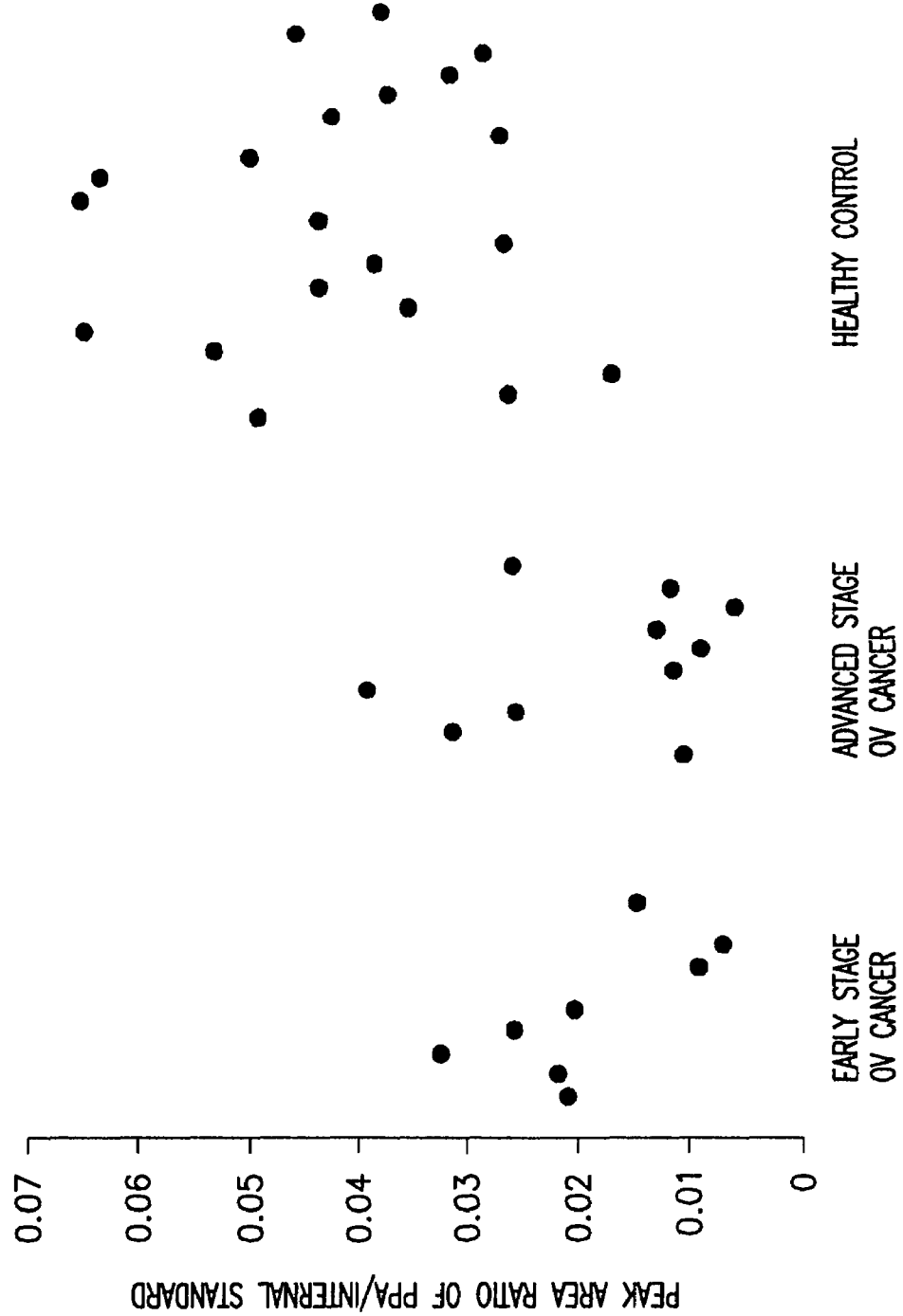
FIG. 5 is a graphical representation of the levels of 16:0, 18:2 PPA in the following 38 serum samples: early stage ov cancer, advanced stage ov cancer and healthy control.
Figure 6:
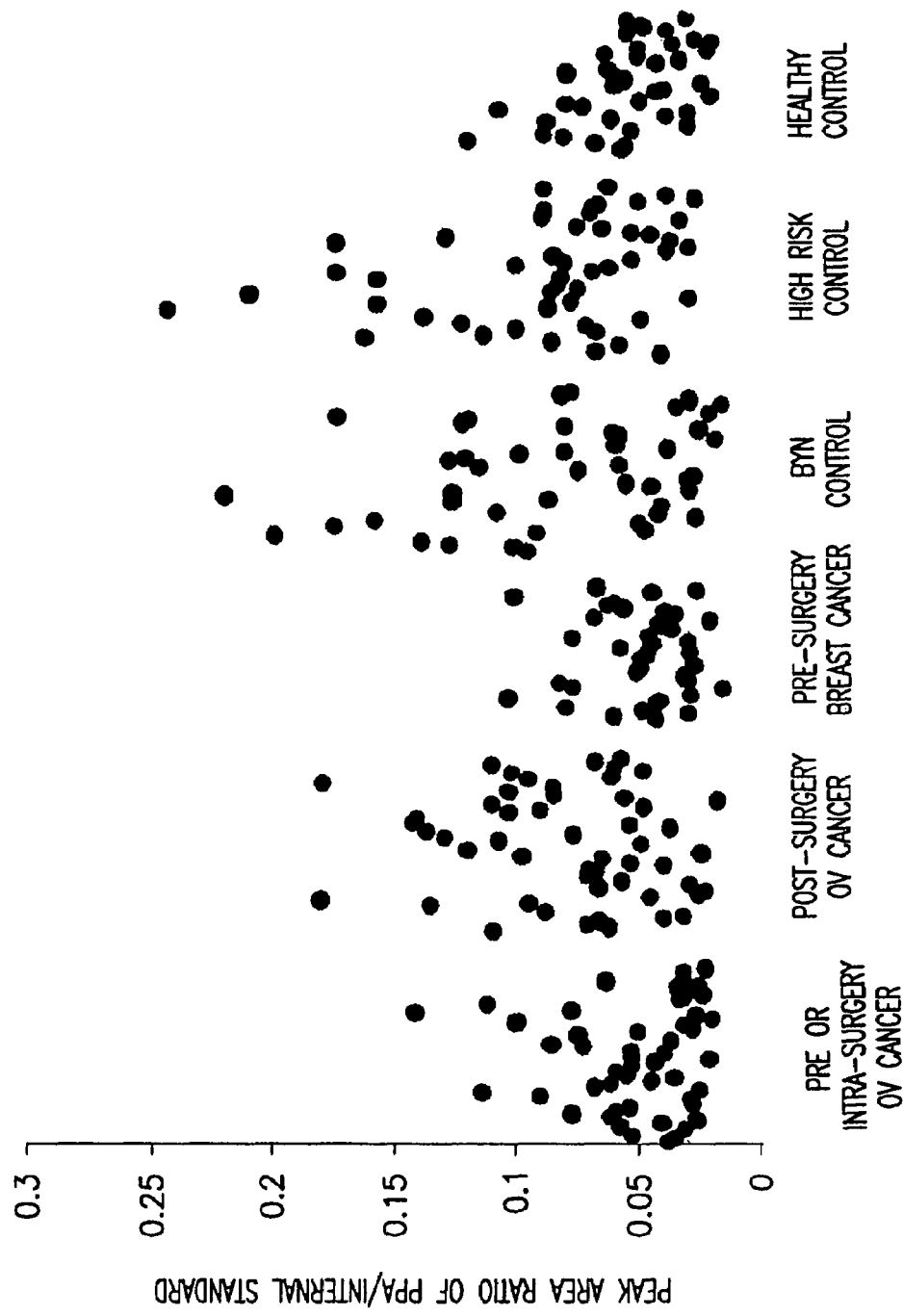
FIG. 6 is a graphical representation of the levels of 16:0, 22:6 PPA in the following 281 plasma samples: pre- or intra-surgery ov cancer, post-surgery ov cancer, pre-surgery breast cancer, benign gynecological disease ("BYN") control, high-risk control and healthy control.
Figure 7:
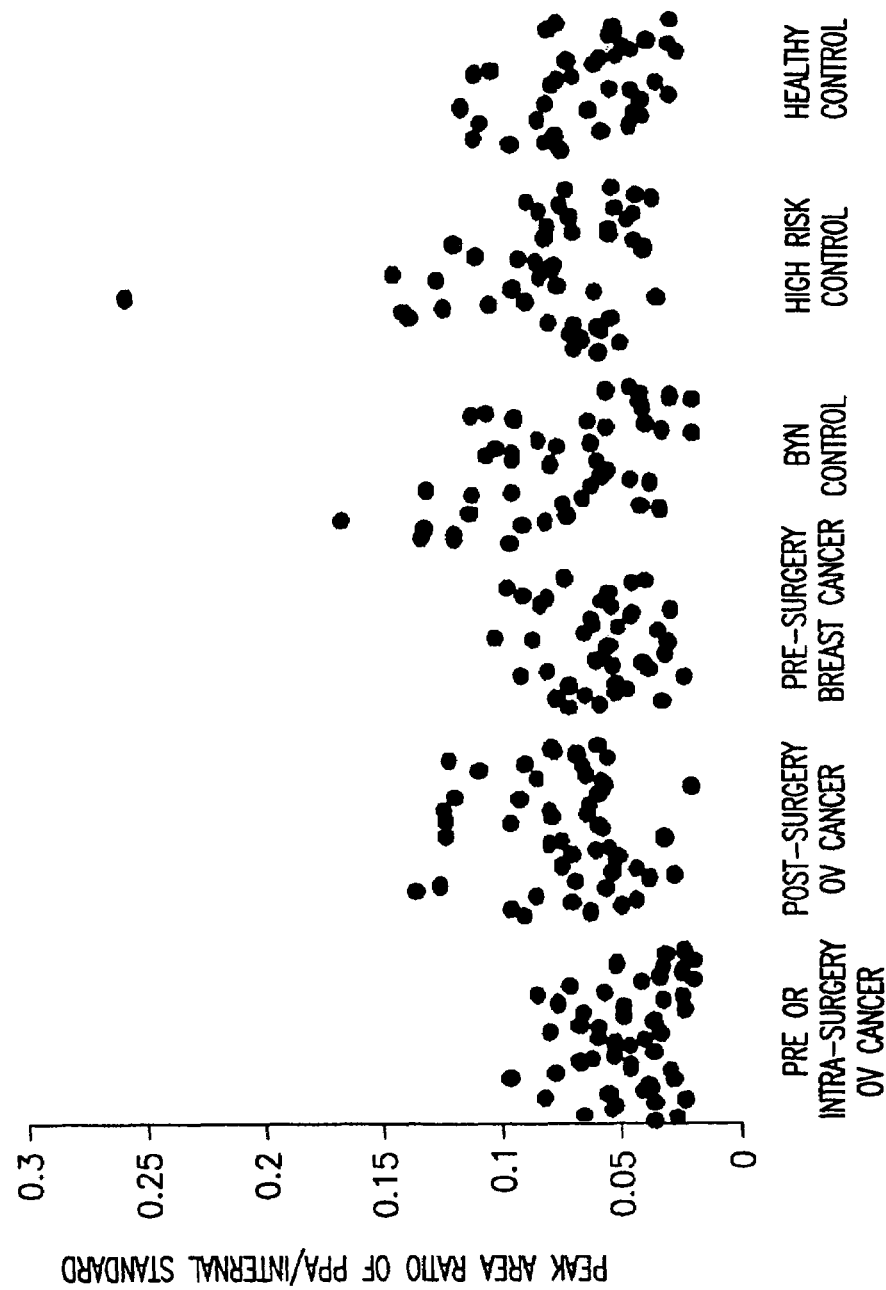
FIG. 7 is a graphical representation of the levels of 16:0, 20:4 PPA in the following 281 plasma samples: pre- or intra-surgery ov cancer, post-surgery ov cancer, pre-surgery breast cancer, benign gynecological disease ("BYN") control, high-risk control and healthy control.
Figure 8:
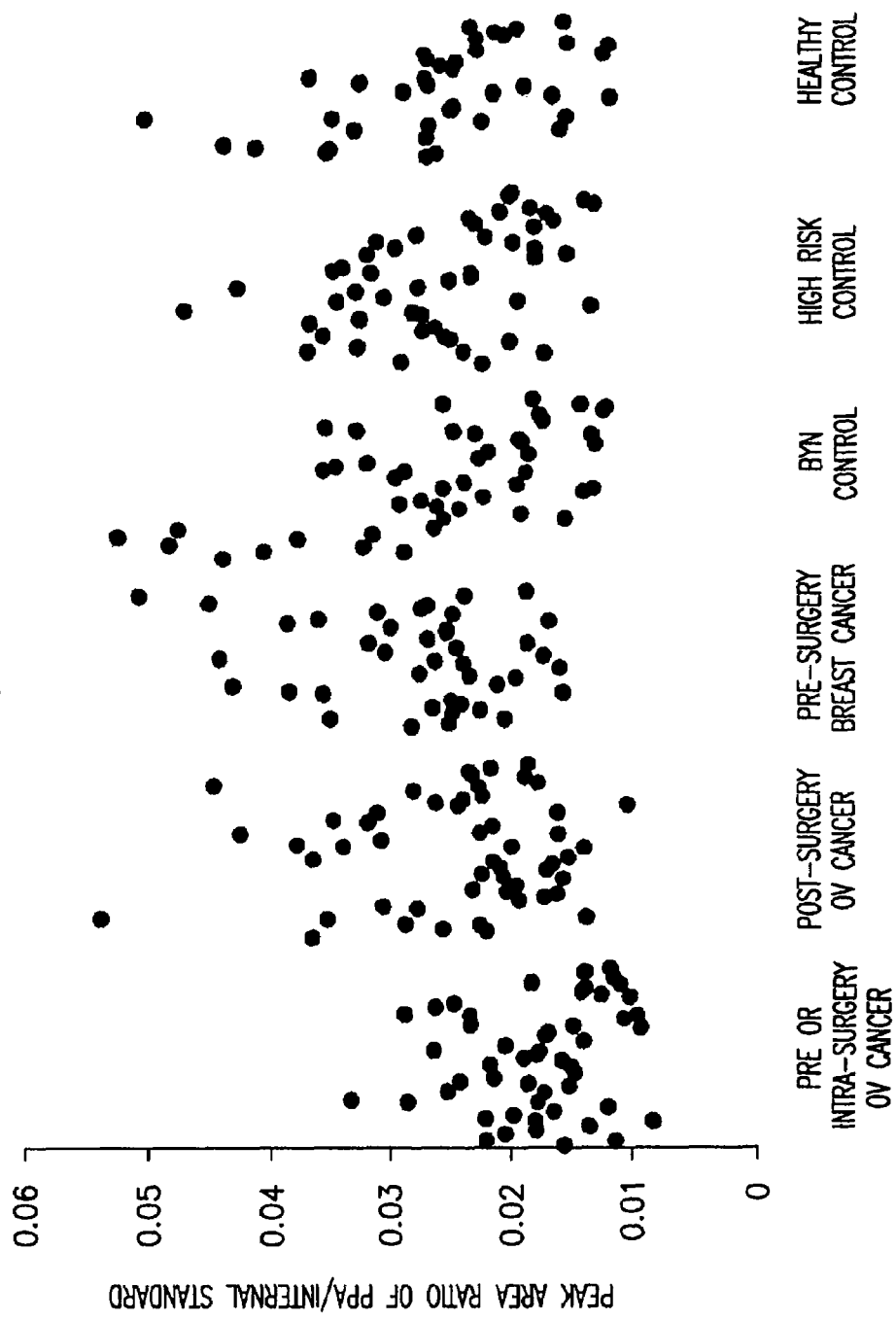
FIG. 8 is a graphical representation of the levels of 16:0, 18:1 PPA in the following 281 plasma samples: pre- or intra-surgery ov cancer, post-surgery ov cancer, pre-surgery breast cancer, benign gynecological disease ("BYN") control, high-risk control and healthy control.
Figure 9:
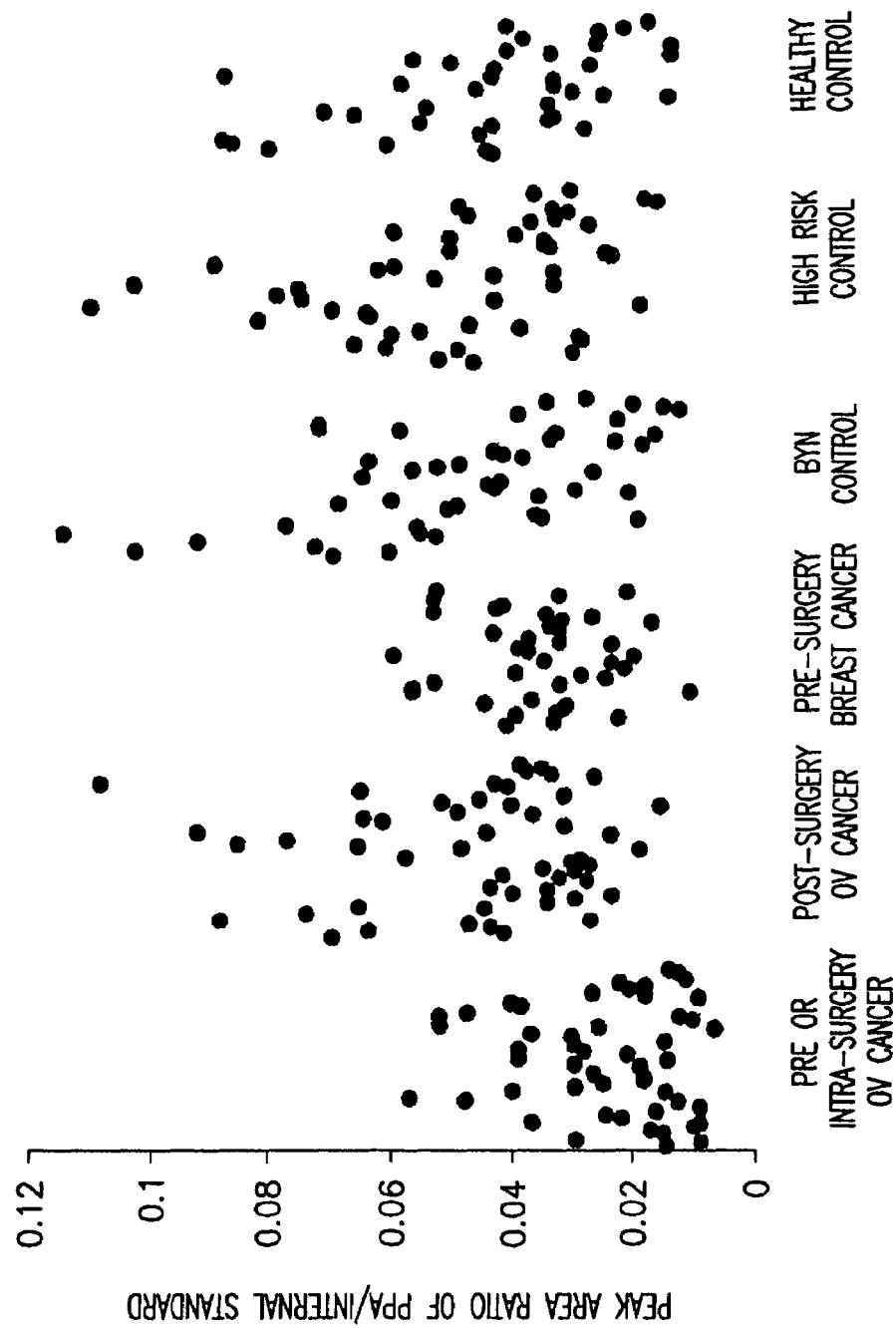
FIG. 9 is a graphical representation of the levels of 16:0, 18:2 PPA in the following 281 plasma samples: pre- or intra-surgery ov cancer, post-surgery ov cancer, pre-surgery breast cancer, benign gynecological disease ("BYN") control, high-risk control and healthy control.

Embodiments of the invention concern methods of detecting or screening for ovarian cancer in a female test subject involving determination of the amount of plasmenyl-PA or a biomarker having a mass charge ratio of approximately 655.3, i.e., a mass charge ratio of 655.3 or close to 655.3, in a bodily fluid of the female test subject.

Plasmalogens are a class of phospholipids characterized by the presence of a vinyl-ether bond present at the sn-1 position of the glycerol backbone, rather than an ester bond as in diacylglycerophospholipids. The sn-2 position is occupied by a fatty acid.

Moderate amounts of plasmalogens are found in the kidneys, skeletal muscles, the spleen and blood cells. The biological functions of plasmalogens are not clear. It is considered that plasmalogens play the following roles in the human body:

preventing oxidation, mediating membrane dynamics, acting as storage depots of fatty acids, and serving as lipid mediators.

Plasmenyl-PA (phosphatidic acid plasmalogen) ("PPA") is a class of plasmalogen with a phosphatidic acid group attached to the sn-3 position of the glycerol backbone. To date, there is no report to show that plasmenyl-PA is present in biological systems.

The structure of plasmenyl-PA is as follows:

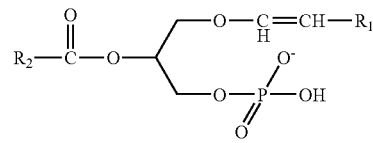

In the above structure, $R_1$ and $R_2$ are alkyl chains.

Plasmenyl-PA that can be used in the methods disclosed herein can include any combination of the following ratios of number of carbon atoms to number of double bonds connecting the carbon atoms: at the sn-1 position, 12:1, 14:1, 16:1, 16:2, 18:1, 18:2, 18:3, 18:4, 20:1, 20:5, 22:1 and 22:7; at the sn-2 position, 12:0, 14:0, 16:0, 16: 1, 18:0, 18:1, 18:2, 18:3, 20:0, 20:4, 22:0 and 22:6.

Non-limiting examples of plasmenyl-PA compounds which are sought to be detected in the methods disclosed herein include the following:

16:0, 18:2 PPA,

16:0, 20:4 PPA,

16:0, 22:6 PPA and

16:0, 18:1 PPA.

By using electrospray mass spectrometry, experimental evidence was obtained that showed that plasmenyl-PA is present in human plasma or serum.

In preferred embodiments of the methods disclosed herein, 16:0, 18:1-plasmenyl-PA, 16:0, 18:2-plasmenyl-PA, 16:0, 20:4-plasmenyl-PA or 16:0, 22:6-plasmenyl-PA is sought to be detected. In a most preferred embodiment of the methods disclosed herein, 16:0, 18:2-plasmenyl-PA is sought to be detected.

In the methods disclosed herein, the amount of plasmenyl-PA or a biomarker having a mass charge ratio of approximately 655.3 (considered to be associated with 16:0, 18:2 plasmenyl-PA) in a sample of a bodily fluid taken from a female test subject is compared to a range of amounts of plasmenyl-PA or the biomarker found in samples taken from a group of normal female subjects of the same species as the female test subject, and lacking ovarian cancer (e.g., if the female test subject is a human, then a normal female subject is a human female who does not have ovarian cancer). The number of normal female subjects (not having ovarian cancer) in the group should be sufficient to establish a "normal" range for plasmenyl-PA or the biomarker. A lower amount of the plasmenyl-PA or the biomarker in the sample of the bodily fluid taken from the female test subject when compared to the range of amounts of plasmenyl-PA or the biomarker in the samples of the bodily fluid taken from the group of normal female subjects indicates the presence of ovarian cancer.

The amount of plasmenyl-PA or the biomarker having a mass charge ratio of approximately 655.3 detected in the sample taken from the female test subject may be measured by first extracting lipids as described in detail infra. The amount of plasmenyl-PA or the biomarker having a mass charge ratio of approximately 655.3 is then quantified using standard procedures, such as mass spectroscopy, gas chromatography, HPLC, NMR or other approaches.

In addition to the direct measurement of the plasmenyl-PA or the biomarker having a mass charge ratio of approximately 655.3 by extraction, antibodies, such as monoclonal antibodies reactive with plasmenyl-PA or the biomarker having a mass charge ratio of approximately 655.3 can be used in an assay to detect the amount of plasmenyl-PA or the biomarker having a mass charge ratio of approximately 655.3 in a test sample. For example, anti-plasmenyl-PA (or anti-biomarker) antibodies may be labeled using standard procedures and used in assays including radioimmunoassays (RIA), both solid and liquid phase, fluorescence-linked assays or enzyme-linked immunosorbent assays (ELISA), wherein the antibody is used to detect the presence and amount of the plasmenyl-PA (or the biomarker having a mass charge ratio of approximately 655.3) in the fluid sample.

The test subject can be an eukaryotic organism, preferably a vertebrate, including, but not limited to, a mammal, a bird, a fish, an amphibian or a reptile. Preferably, the subject is a mammal, most preferably a human. The bodily fluid includes, but is not limited to, plasma, serum, urine, saliva, ascites, cerebral spinal fluid or pleural fluid. Preferably, the bodily fluid is plasma or serum which is obtained from a whole blood specimen from the female test subject.

The methods disclosed herein are non-invasive and require only a bodily fluid specimen, such as a blood specimen from the female test subject (patient). Thus, such methods are useful for screening female patients who have not been previously diagnosed as having ovarian cancer or who are patients who are at risk for developing ovarian cancer. Such patients include women at elevated risk by virtue of a family history of the disease, premenopausal women with anovulatory cycles, and postmenopausal women. The methods disclosed herein thus include a screening test for identifying within a risk population, a subset population with a greater propensity for developing ovarian cancer.

The methods disclosed herein can provide a number of benefits. First, the methods provide a rapid and economical screen for large numbers of female subjects to promote early diagnosis of ovarian cancer, which can result in improved quality of life and better survival rates for patients.

Using the methods disclosed herein for prognosis, the medical professional can determine the appropriate course of therapy for a female having ovarian cancer. The methods disclosed herein can also serve to identify female subjects who may not benefit from a particular form of therapy, e.g., surgery, chemotherapy, radiation or biological therapies. Such information could result in an improved therapy design for obtaining better responses to therapy.

Methods disclosed herein can also be used to identify patients for whom therapy should be altered from one therapeutic agent to another. This could obviate the need for "second look" invasive procedures to determine the patient's response to the therapy and facilitate decisions as to whether the particular type of therapy should be continued, terminated or altered.

Because ovarian cancer may recur in a significant number of patients with advanced ovarian cancer, early detection and continued monitoring over time using the methods of the present invention could identify early occult (i.e., "hidden") recurrences prior to symptoms presenting themselves.

In addition, methods disclosed herein will facilitate distinguishing benign from malignant ovarian tumors. Masses in the ovary may be initially detected using procedures such as ultrasound or by physical examination. Thereafter, the method disclosed herein can be used to diagnose the presence of ovarian cancer. This could obviate the need for surgical intervention, and/or identify female subjects where continued monitoring is appropriate, resulting in improved early detection and survival for ovarian cancer patients.

The above-described methods for monitoring of ovarian cancer can be used for either a first detection/diagnosis of ovarian cancer or for detecting the recurrence of ovarian cancer after ovarian cancer surgery or other treatment for ovarian cancer. Such monitoring methods can thus be employed to follow the state of a patient's ovarian cancer. During an ovarian cancer treatment regime, it might be found that amounts of plasmenyl-PA increase or decrease. This can be utilized as a tool for judging the effectiveness of the therapy, e.g., plasmenyl-PA levels would rise if the patient is responding.

As discussed hereinafter, levels of plasmenyl-PA were quantified in both human serum and human plasma, and it was found that 16:0, 18:2-plasmenyl-PA is a diagnostic biomarker for ovarian cancer. In one study using 196 serum samples, it was found that if 16:0, 18:2-plasmenyl-PA is used as the diagnostic marker, the sensitivity for ovarian cancer was 86% and the specificity for controls was 86.7%, with a positive predictive value of 86.5%. In a second study using 38 serum samples, it was found that if 16:0, 18:2-plasmenyl-PA is used as a diagnostic marker, 7 of the 8 of the early stage ovarian cancer samples and 8 of the 10 of the advanced stage ovarian cancer samples can be detected. The sensitivity for ovarian cancer was 83% and the specificity for controls was 95%, with a positive predictive value of 89.5%.

In a third study using 229 plasma samples, it was found that if 16:0, 18:2-plasmenyl-PA is used as the diagnostic marker, the sensitivity for ovarian cancer was 76.5% and the specificity for controls was 74.5%, with a positive predictive value of 75%.

EXAMPLES

The invention will now be described in the context of the following non-limiting examples.

Example 1

Example 1 (a)

Preparation of Plasmenyl-PA from Plasmenyl-PC 0.6 μmol of plasmenyl-PC were placed into 90 μl of 50 mM Tris-HCl buffer, 10 mM $CaCl_2$, 1% triton (pH 8.0) and sonicated for 10 minutes. 5 μl of PLD enzyme (10 units, 1 unit will liberate 1.0 μM of choline from L-α-phosphatidylcholine (egg yolk) per hour at pH 5.6 at 30° C.) were added and the reaction was carried out for 4 hours at 37° C. The reaction was stopped by adding 0.4 ml of the extraction solvent, chloroform/methanol (2:1, v/v). A Bligh-Dyer extraction was performed and the organic phase and the aqueous phase were dried under $N_2$ respectively. See the following reaction scheme:

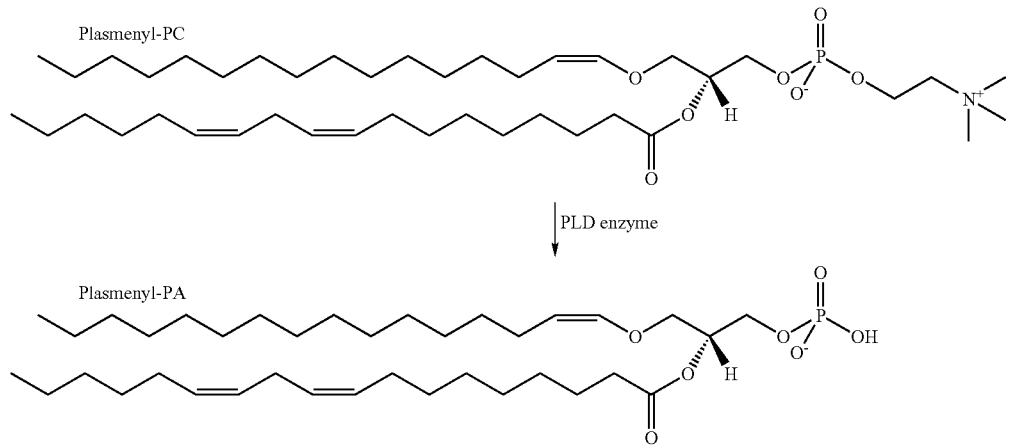

A crude plasmenyl-PA product was thus obtained and a mass spectrometric experiment was done to get the MRM (multiple reaction monitoring) transitions for plasmenyl-PA.

Example 1 (b)

Extraction of Lipids from Plasma or Serum Samples

Lipid extraction was done according to the following procedure: Add 100 μl 2 μg/ml 1, 2-diphytanoyl-sn-glycerol-3-phosphate, the internal standard for the assay, into 400 μl plasma or serum samples. Vortex and add 2 ml 2:1 methanol-chloroform into the samples. Vortex again and centrifuge the mixture for 5 minutes at 4000 rpm and 10° C. Transfer the upper liquid layer into a test tube and dry the liquid layer under nitrogen. Then add 200 μl 0.1 M ammonium acetate in methanol into the nitrogen-dried lipids. Vortex and transfer everything in the test tube into a microcentrifuge tube. Centrifuge at 9000 rpm for 5 minutes. Transfer the supernatant into an injection vial for MRM LC/ESI/MS/MS (liquid chromatography/electrospray ionization/tandem mass spectroscopy) analysis.

Example 1 (c)

LC/ESI/MS/MS Analysis

MRM LC/ESI/MS/MS analysis of the plasmenyl-PA compound from Example 1(b) was performed using a Quatro micro mass spectrometer (Micromass, Altrincham, U.K.) equipped with an electrospray ionization (ESI) probe and interfaced with a Shimadzu SCL-10AvpHPLC system (Shimadzu, Tokyo, Japan). Lipids were separated with a Betabasic-18 column (20+2.1 mm, 5 μm, Thermo Electron, Waltham, Mass.), protected by a Betabasic 18 pre-column (10×2.1 mm, 5 μm, Thermo Electron, Waltham, Mass.). 300 μM ammonium phosphate, pH=5.46 buffer was used as mobile phase A, while 9:1 (v:v) methanol-acetonitrile was used as mobile phase B. The gradient used was as follows: the column was first equilibrated with 70% B (30% A), followed by a linear change from 70% B (30% A) to 100% B (0% A) at 200 μl/minutes in the first 5 minutes. The gradient was kept at 100% in the following 3 minutes. Then it was changed back to 70% B (30% A) to re-equilibrate the column. The flow rate was 200 μl/minutes. Mass spectrometric analyses were performed online using electrospray ionization/tandem mass spectrometry in the negative multiple reaction monitoring (MRM) mode (capillary voltage: 3.0 KV; cone potential: 55 V; collision energy: 25 eV). The MRM transitions used to detect plasmenyl-PA were the mass charge ratio for the molecular anion M- and its daughter ion (m/z of 375.2).

Example 1 (d)

Samples and Statistical Analysis 196 serum samples were collected. The serum samples were divided into five groups: pre-surgery ovarian ("ov") cancer samples, post-surgery ovarian ("ov") cancer samples, benign gynecological disease control samples, high-risk control samples, and healthy control samples. Data analysis was done using the student t-test.

Example 1 (e)

Results

The levels of 16:0, 18:2 plasmenyl-PA in 196 serum samples were analyzed using the LC/ESI/MS/MS method described above. The results are shown in Table 1 and FIG. 1.

The levels of plasmenyl-PA were expressed as a peak area ratio of plasmenyl-PA/internal standard. As expected, the levels of 16:0, 18:2 plasmenyl-PA in the post-surgery ovarian cancer samples were much higher than the levels of 16:0, 18:2 plasmenyl-PA in the pre-surgery ovarian cancer samples, with a p-value =0.03, meaning that surgery can affect the levels of 16:0, 18:2 plasmenyl-PA in ovarian cancer patients. It is considered that the level of plasmenyl-PA is inversely proportionate to tumor size. Therefore, the levels of 16:0, 18:2 plasmenyl-PA can be used as a prognostic tool for ovarian cancer patients with treatment. The levels of 16:0, 18:2 plasmenyl-PA in the control samples were also much higher than pre-surgery ovarian cancer patients. The p values for the benign gynecological disease control, high-risk control, and healthy controls related to pre-surgery ovarian cancer patients were all less than 0.00001. If 0.056 is used as the cut-off, the levels of 16:0, 18:2 plasmenyl-PA in 4 of 29 pre-surgery ovarian cancer patients were above this value, with the sensitivity equaling 86%. The levels of 16:0, 18:2 plasmenyl-PA in 49 of 58 benign gynecological disease controls were above this value, with the specificity equaling 84%. The levels of 16:0, 18:2 plasmenyl-PA in 29 of 35 high-risk controls were above this value, with the specificity equaling 83%. The levels of 16:0, 18:2 plasmenyl-PA in 28 of 29 healthy controls were above this value, with the specificity equaling 96%.

TABLE 1

Level of 16:0, 18:2 plasmenyl-PA, Standard Deviation, and p Value (related to pre-surgery ovarian cancer patients) in Serum Samples, as determined by peak area ratio of analyte to internal standard

| Serum sample | Average Level of 16:0, 18:2 plasmenyl-PA | Standard deviation | p value |
|---|---|---|---|
| Pre-surgery ovarian cancer | 0.047 | 0.037 | — |
| Post-surgery ovarian cancer | 0.066 | 0.033 | 0.03 |
| Benign gynecological disease | 0.097 | 0.048 | <0.00001 |
| High risk | 0.102 | 0.053 | <0.00001 |
| Healthy controls | 0.107 | 0.054 | <0.00001 |

Example 2

Example 2 (a)

Samples 38 serum samples were collected. These serum samples were divided into the following three groups: pre-surgery early stage ovarian ("ov") cancer samples, pre-surgery advanced stage ovarian ("ov") cancer samples, and healthy control samples.

Example 2 (b)

Results

The levels of 16:0, 22:6 plasmenyl-PA, 16:0, 20:4 plasmenyl-PA, 16:0, 18:1 plasmenyl-PA, and 16:0, 18:2 plasmenyl-PA in 38 serum samples were analyzed using the LC/ESI/MS/MS method described above. The results are shown in FIG. 2, FIG. 3, FIG. 4, and FIG. 5 respectively. Among these four species of plasmenyl-PA, 16:0, 18:2 plasmenyl-PA gave the best result to diagnose ovarian cancer. If 0.026 was used as the cutoff, 7 of the 8 of early stage of ovarian cancer were below the cutoff, with a sensitivity=87.5%, 8 of the 10 advanced stage ovarian cancer were below the cutoff, with a sensitivity=80%. 19 of the 20 healthy controls were above the cutoff, with a specificity=95%.

Example 3

Example 3 (a)

Samples and Statistical Analysis 229 plasma samples were collected. The plasma samples were divided into the following six groups: pre-surgery ovarian ("ov") cancer samples, post-surgery ovarian ("ov") cancer samples, pre-surgery breast cancer samples, high-risk control samples, benign gynecological disease control samples and healthy control samples. Data analysis was done using the student t-test.

Example 3 (b)

Results

The levels of 16:0, 22:6 plasmenyl-PA, 16:0, 20:4 plasmenyl-PA, 16:0, 18:1 plasmenyl-PA, and 16:0, 18:2 plasmenyl-PA in 229 plasma samples were analyzed using the LC/ESI/MS/MS method described above. The results are shown in FIG. 6, FIG. 7, FIG. 8, FIG. 9, respectively, and the following Table 2. Among these four species of plasmenyl-PA, 16:0, 18:2 plasmenyl-PA gave the best results to diagnose ovarian cancer.

If 0.03 is used as the cutoff, 12 of 51 pre-surgery ovarian cancer patients are above the cutoff, with a sensitivity=76.5%. 11 of 41 of the breast cancer patients are below the cutoff, with a specificity=73.2%. 11 of 50 of the high-risk controls are below the cutoff, with a specificity=78%. 12 of 47 of the benign gynecological disease controls are below the cutoff, with a specificity=74.5%. 12 of 40 of the healthy controls are below the cutoff, with a specificity=70%.

The results obtained using the plasma samples were not as good as the results obtained using the serum samples. Due to the possibility that plasma samples were contaminated by platelets, it is not unusual that the results for the serum samples were better than the results for the plasma samples.

TABLE 2

Level of 16:0, 18:2 plasmenyl-PA, Standard Deviation, and p Value in Plasma Samples, as determined by peak area ratio of analyte to internal standard

| Plasma sample | Average Level of 16:0, 18:2 plasmenyl-PA | Standard deviation | p value (related to pre-surgery ov cancer) |
|---|---|---|---|
| Pre-surgery ovarian cancer | 0.0241 | 0.0187 | — |
| Post-surgery ovarian cancer | 0.0452 | 0.0191 | <0.00001 |
| Pre-surgery breast cancer | 0.0343 | 0.0128 | 0.00015 |
| Benign gynecological disease | 0.0464 | 0.0216 | <0.00001 |
| High risk | 0.0456 | 0.0183 | <0.00001 |
| Healthy controls | 0.0402 | 0.0245 | <0.00001 |

What is claimed is:

1. A method of detecting ovarian cancer in a female test subject comprising:
   determining the amount of plasmenyl-PA in a sample of a bodily fluid selected from the group consisting of plasma and serum taken from a female test subject being screened for ovarian cancer, and
   comparing the amount of plasmenyl-PA in the sample of the bodily fluid taken from the female test subject to a range of amounts of plasmenyl-PA found in samples of said bodily fluid taken from a group of normal female subjects of the same species as the female test subject and lacking ovarian cancer, whereby a lower amount of the plasmenyl-PA in the sample of the bodily fluid taken from the female test subject indicates the presence of ovarian cancer.

2. The method of claim 1, wherein the female test subject is a human.

3. The method of claim 2, wherein the plasmenyl-PA is selected from the group consisting of 16:0, 18:2 PPA; 16:0, 20:4 PPA; 16:0, 22:6 PPA; and 16:0, 18:1 PPA.

4. The method of claim 2, wherein the plasmenyl-PA is 16:0, 18:2 PPA.

5. A method for monitoring ovarian cancer in a female test subject over time comprising:
   (a) determining the amount of plasmenyl-PA in a sample of a bodily fluid selected from the group consisting of plasma and serum taken from a female test subject at a first time, (b) determining the amount of plasmenyl-PA in a sample of said bodily fluid taken from said female test subject at a second time, which is a later time than the first time, (c) comparing the amounts of plasmenyl-PA in step (a) and step (b) to determine whether there has been an increase or a decrease in the amount of plasmenyl-PA in the sample taken from the female test subject at the later time relative to the amount of the plasmenyl-PA in the sample taken from the female test subject at the first time, whereby a decrease in the amount of the plasmenyl-PA in the sample of the bodily fluid from the later time indicates the presence of, or worsening of, ovarian cancer, or an increase in the amount of plasmenyl-PA in the sample of the bodily fluid from the later time indicates an absence, or improvement of, ovarian cancer.

6. The method of claim 5, wherein the test subject is a human.

7. The method of claim 6, wherein the plasmenyl-PA is 16:0, 18:2 PPA; 16:0, 20:4 PPA; 16:0, 22:6 PPA; and 16:0, 18:1 PPA.

8. The method of claim 6, wherein the plasmenyl-PA is 16:0, 18:2 PPA.

9. The method of claim 6, wherein the method is for detection of recurrence of ovarian cancer after therapy or surgery to treat ovarian cancer.

* * * * *